(12) United States Patent
Lee et al.

(10) Patent No.: US 7,118,914 B2
(45) Date of Patent: Oct. 10, 2006

(54) METHOD FOR PRODUCING HUMAN LACTOFERRIN IN PLANT CELL CULTURE

(75) Inventors: Haeng-Soon Lee, Daejeon-si (KR); Sang-Soo Kwak, Daejeon-si (KR); Suk-Yoon Kwon, Daejeon-si (KR); Dae-Yeul Yu, Daejeon-si (KR); Jae Whune Kim, Daejeon-si (KR); Ok-Sun Lee, Daejeon-si (KR)

(73) Assignee: Korea Research Institute of Bioscience and Biotechnology, Daejeon-Si (KR)

( * ) Notice: Subject to any disclaimer, the term of this patent is extended or adjusted under 35 U.S.C. 154(b) by 403 days.

(21) Appl. No.: 10/396,658

(22) Filed: Mar. 25, 2003

(65) Prior Publication Data

US 2004/0040062 A1    Feb. 26, 2004

(30) Foreign Application Priority Data

Apr. 23, 2002    (KR) .................... 10-2002-0022272

(51) Int. Cl.
*C12N 15/82*    (2006.01)
*A01H 4/00*    (2006.01)

(52) U.S. Cl. .................. 435/419; 435/414; 435/252.2; 435/252.3

(58) Field of Classification Search ............ 435/252.3, 435/320.1, 410, 414, 419; 80/298, 317.3; 800/298, 317.3
See application file for complete search history.

(56) References Cited

U.S. PATENT DOCUMENTS 6,096,546 A * 8/2000 Raskin ................. 435/410

FOREIGN PATENT DOCUMENTS

WO    WO 01/31018    * 5/2001

OTHER PUBLICATIONS

Salmon V. et al. Production of human lactoferrin in transgenic tobacco plants. Protein Expr Purif. Jun. 1998; 13(1):127-35.*
Gallie D. et al. The tobacco etch viral 5' leader and poly(A) tail are functionally synergistic regulators of translation. Gene. Nov. 20, 1995; 165(2):233-8.*
Choi Y. et al. Rapid and efficient Agrobacterium-mediated transformation of Panax ginseng by plasmolyzing pre-treatment of cotyledons. Plant Cell Rep. (2001) 20:616-621.*
Mitra, et al., Expression of a Human Lactoferrin cDNA in Tobacco Cells Produces Antibacterial Proteins(s), Plant Physiol. 106:977-981, 1994.
Chong, et al., Expression of full-length bioactive antimicrobial human lactoferrin in potato plants, Transgenic Research 9: 71-78, 2000.
Salmon, et al., Production of Human Lactoferrin in Transgenic Tobacco Plants, Protein Expression and Purification 13, 127-135, 1998.
Arakawa, et al., Improvements in Human Health Through Production of Human Milk Proteins in Transgenic Food Plants, edited by Shahidi, et al., Chemicals via Higher Plant Bioengineering, Kluwer Academic/Plenum Publishers,NY, 149—149, 1999.

* cited by examiner

*Primary Examiner*—Cynthia Collins
(74) *Attorney, Agent, or Firm*—Lucas & Mercanti, LLP

(57) ABSTRACT

The present invention relates to a method for producing target protein in plant cell culture, more particularly to the method for producing target protein comprising the steps of i) constructing vector containing SWPA2 promoter and gene for the target protein, ii) introducing said vector into *Agrobacterium*, iii) transforming said *Agrobacterium* into plant cell, and iv) mass-producing target protein using said transformed plant cells. The method of the present invention can mass-produce target proteins such as human lactoferrin. Moreover, the transformed plant can also be used to make health foods when medicinal plant is used as a host cell.

3 Claims, 15 Drawing Sheets

METHOD FOR PRODUCING HUMAN LACTOFERRIN IN PLANT CELL CULTURE

This patent application claims a benefit of priority from Korean Patent Application No. 2002-22272 filed Apr. 23, 2002, the contents of which is incorporated herein by reference.

FIELD OF THE INVENTION

The present invention relates to a method for producing target protein using high-expressing peroxidase promoter (SWPA2), more particularly to a method for producing target protein comprising the steps of i) constructing expression vector containing SWPA2 promoter and gene for the target protein, ii) introducing said vector into *Agrobacterium*, iii) transforming said *Agrobacterium* into plant cell, and iv) mass-producing target protein using said transformed plant cells. The present invention provides the method for mass production of target protein such as human lactoferrin. Moreover, the transformed plant can also be used to make health foods when medicinal plant is used as a host cell.

BACKGROUND OF THE INVENTION

The present invention relates to a method for producing target protein using high-expressing peroxidase promoter (SWPA2), more particularly to a method for mass-producing target protein that comprises the steps of constructing expression vector expressing the target protein using SWPA2, transforming *Agrobacteria* with the expression vector, developing transformant into which the *Agrobacteria* is introduced and mass-producing target protein using the transformant.

Domestic (Korean) wild medicinal plants of Araliaceae family (*Panax ginseng*, Siberian ginseng, *Dendropanax morbifera*, etc) have various physiological activities such as enhancing immune response and cellular defense, anti-cancer, anti-oxidant, anti-lipid peroxidation, anti-microorganism activity, etc. Especially, Korean wild medicinal plants of Araliaceae family have much greater content of many active ingredients having excellent biological activity than any other cultivated in foreign countries.

Human lactoferrin is included in milk of human with high concentration. As a glycoprotein bound with iron, human lactoferrin has 80-kDa molecular weight and consists of two lobes. Each lobe has one iron-binding site (Metz-Boutigue et al., *Eur. J. Biochem.*, 145, 659–676, 1984). Lactoferrin has many beneficial physiological activities and is related to various cellular defense mechanisms such as bacteriocidal and bacteriostatic action, regulation of cell proliferation, suppression of peroxy-lipid formation, regulation of immune system, regulation of iron-absorption, suppression of inflammation in infected area, anti-virus activity, prevention of *E.coli* from attaching to intestine cells, proliferation of *Lactobacillus*, etc (Yu, *Korean Dairy Techno.*, 15, 83–89, 1997). Major products containing lactoferrin are exemplified by powdered milk for infants, cosmetics, food additives, anti-diarrhea remedies, peritoneal dialysis agents, clinical nutrition agents, hygienic products for women, medicines for the eyes, gums, etc (Nam et al., *Korean J. Dairy Sci.*, 18, 289–298, 1996; Tomita, 1999, Morinaga Milk Industry Co., Ltd).

The production of valuable materials in plant cell cultures has been limited to plant-originated low-molecular substances taxol, shikonin, etc). But, recently, applicable area is enlarged in various fields due to the development of plant bioreactor. For example, Nitto Denko Co. produced ginseng culture cells (cultured in 20 ton tank) as a health food in Japan and Microplants Co. produced cultivated seedlings of Siberian ginseng (U.S. Pat. #09/578). In addition, the present inventors mass-produced peroxidase in sweetpotato cell cultures (Korea patent #1997-117516), isolated peroxidase genes expressed highly in culture cells (Korea patent #1998-176420) and developed high-expressing peroxidase SWPA2 promoter (PCT application #PCT/KR00/01231), leading to the development of industrial culture cell lines and the production of useful substances from the culture cells.

In regard to the production of human lactoferrin from plants or plant cell cultures, there have been reported that 48 kDa human lactoferrin-derived peptide was produced (1.8% of total water-soluble proteins) in transformed tobacco callus using CaMV 35S promoter (Mitra and Zhang, *Plant Physiol.*, 106, 977–981, 1994), human lactoferrin was produced in tobacco plant leaves (0.3% of total protein; Salmon et al., *Protein Express. Purif.*, 13, 127–135, 1998), in potato tuber (0.1% of total water-soluble protein) using mas P2 promoter (Chong et al., *Transgenic Res.*, 9, 71–78, 2000), in sweetpotato callus and storage roots, potato tuber and tobacco plant (0.04–0.07% of total water-soluble protein) using CaMV 35S promoter (Liu et al., Research Report, Ministry of Science and Technology, Korea, 2000). A rice plant producing human lactoferrin (500 μg/g polished rice) by regulating rice glutelin promoter was also reported (Anzai et al., Lactoferrin: Structure, *Function Appli.*, 265–271, 2000). However, the mass-production of human lactoferrin especially in a specific culture period using high-expressing promoter has not been reported yet.

High-expressing peroxidase promoter is a peroxidase promoter (SWPA2) induced by oxidative stress and is highly expressed in suspension culture cells of sweetpotato (PCT application #PCT/KR00/01231). The promoter showed 30-fold higher activity than CaMV 35S promoter, which was confirmed by transient assay with GUS protein using tobacco protoplasts. In addition, the promoter is expressed in tobacco plant and culture cells and especially, highly expressed in suspension culture cells of transformed tobacco in the late stage of logarithmic growth phage. The promoter is not expressed in normal plant leaves at all but is expressed when it gets oxidative stress such as ozone, low temperature, wounding, etc (Kim et al., *Plant Mol. Biol.*, 51, 831–838, 2003).

Thus, in order to develop plant culture cells mass-producing useful protein such as human lactoferrin, the present inventors prepared plant culture cells that are available for the expression of target protein in intracellular organelles using high-expressing peroxidase SWPA2 promoter. The present inventors have completed the present invention by confirming that the target protein can be mass-produced using the prepared culture cells.

SUMMARY OF THE INVENTION

It is an object of the present invention to provide an expression vector expressing target protein using high-expressing peroxidase promoter (SWPA2), *Agrobacteria* genus microorganism transformed with the expression vector, a transformant mass-producing target protein that is prepared by introducing the *Agrobacteria* genus microorganism into the same, and a method for preparing target protein using the transformant.

DETAILED DESCRIPTION OF THE INVENTION

To achieve the above object, the present invention provides an expression vector expressing target protein using high-expressing peroxidase promoter (SWPA2).

The present invention also provides *Agrobacteria* genus microorganism transformed with the above expression vector.

The present invention further provides a transformant mass-producing target protein that is prepared by introducing the above *Agrobacteria* genus microorganism into the same.

The present invention also provides a method for preparing target protein using the above transformant.

Further features of the present invention will appear hereinafter.

The present invention provides a plant expression vector containing high-expressing peroxidase promoter (SWPA2) and target protein gene, and expressing target protein by the high-expressing peroxidase promoter (SWPA2).

In the present invention, high-expressing peroxidase promoter (SWPA2) (PCT application #PCT/KR00/01231) isolated from sweetpotato culture cells producing a high level of peroxidase was used. The expression of the promoter is induced by oxidative stress and the activity to express target protein is much higher than that of CaMV 35S promoter that has been widely used as a plant transformation.

In order to express target protein, human lactoferrin, the present invention provides a plant expression vector containing high-expressing peroxidase promoter (SWPA2), TEV (tobacco etch virus) leader sequence, signal sequence of calreticulin, human lactoferrin gene and CaMV 35S transcription terminator (see FIG. 1).

We, the present inventors, combined calreticulin signal sequence with human lactoferrin gene to make the expression of the target protein easy and used CaMV 35S transcription terminator as a transcription terminator.

The present invention also provides *Agrobacteria* genus microorganism transformed with the above expression vector in order to produce a transformant mass-producing target protein in plants or culture cells.

In the preferred embodiments of the present invention, the present inventors introduced a plant expression vector containing high-expressing peroxidase promoter (SWPA2), TEV leader sequence, human lactoferrin gene and CaMV 35S transcription terminator into *Agrobacterium tumefaciens* to express human lactoferrin and named the *Agrobacterium* transformed with the above plant expression vector "*Agrobacterium tumefaciens* EHA101 (SWPA2::hLf/ pCGN1578)", which was deposited at Gene Bank of Korea Research Institute of Bioscience and Biotechnology on Apr. 3, 2002 (Accession No: KCTC 10217BP).

The present invention also provides a transformant mass-producing target protein that is prepared by introducing the above *Agrobacteria* genus microorganism into the same.

The present inventors prepared the transformant mass-producing target protein by co-cultivation of the *Agrobacteria* genus microorganism with plants or plant culture cells.

For the above plants, tobacco or medicinal plants of Araliaceae family can be used and especially, it is preferable to select one from a group consisting of Siberian ginseng, *Panax ginseng*, wild ginseng, *Aralia elata* and *Dendropanax morbifera*.

In the preferred embodiments of the present invention, the present inventors prepared a transformant producing human lactoferrin by co-cultivation of *Agrobacteria* genus microorganism (Accession No: KCTC 10217BP) transformed with the expression vector expressing human lactoferrin with tobacco plants or culture cells and named the tobacco culture cells producing human lactoferrin "hLf tobacco BY2 cell line", which was deposited at Gene Bank of Korea Research Institute of Bioscience and Biotechnology on Apr. 3, 2002 (Accession No: KCTC 10218BP). Tobacco BY2 cell line used in the present invention is characterized by fast culture, being suitable for mass-culture and easy purification, making it a preferable model for the production of recombinant protein from plant cell cultures (Fischer et al., *Biotechnol. Appl. Biochem.*, 30, 109–112, 1999). Therefore, the transformant of the present invention is available for the mass-production of human lactoferrin using tobacco BY-2 cell line having fast culture and for the purification of the expressed human lactoferrin.

In the preferred embodiments of the present invention, the present inventors prepared a transformant producing human lactoferrin by co-cultivation of *Agrobacteria* genus microorganism (Accession No: KCTC 10217BP) transformed with the expression vector expressing human lactoferrin with ginseng plant or culture cells. The present inventors named the ginseng culture cells producing human lactoferrin "hLf ginseng cell line" and deposited at Gene Bank of Korea Research Institute of Bioscience and Biotechnology on Apr. 3, 2002 (Accession No: KCTC 10219BP). Ginseng used in the present invention is a highly valuable medicinal plant having excellent physiological activities such as enforcing immune system, etc. Thus, ginseng can be used for the development of highly valuable health food especially when human lactoferrin is massively expressed therein.

The present inventors further prepared a transformant producing human lactoferrin by co-cultivation of *Agrobacteria* genus microorganism (Accession No: KCTC 10217BP) transformed with the expression vector expressing human lactoferrin with Siberian ginseng culture cells, and named the Siberian ginseng culture cells producing human lactoferrin "hLf Siberian ginseng cell line". Siberian ginseng used in the present invention is a highly valuable medicinal plant having excellent physiological activities such as enforcing immune system, etc. Thus, Siberian ginseng can be used for the development of highly valuable health food especially when human lactoferrin is massively expressed therein.

The present invention also provides health food containing the transformant producing human lactoferrin as an active ingredient.

Lactoferrin is a very beneficial protein having various physiological activities such as bacteriocidal and bacteriostatic action, regulation of cell proliferation, suppression of peroxy-lipid formation, regulation of immune system, regulation of iron-absorption, suppression of inflammation in infected area, anti-virus activity, prevention of *E.coli* from attaching to intestine cells, proliferation of *Lactobacillus bifidus*, etc. Thus, the extract of the transformant of the present invention producing human lactoferrin can be effectively used for the preparation of health food.

It is very useful for the production of health food to use a transformant prepared by medicinal plants of Araliaceae family (*Panax ginseng*, Siberian ginseng, *Dendropanax morbifera*, etc) owing to their physiological activities such as enforcing immune response and cellular defense, anti-cancer, anti-oxidant, anti-lipid peroxidation, anti-microorganism activity along with the activities that human lactoferrin has.

The transformant of the present invention can be extracted using water or alcohol, and the extract can be used for the production of health food by being added as it is or with other eatable ingredients following the conventional methods. In general, the extract can be added 0.001–50 weight % to raw material and adding 0.01–5 weight % is more preferred for the production of health food or drink. There is no limit in health food that can be prepared with the extract. For example, meat, sausage, bread, chocolate, candy, snack, cookies, pizza, rameyon, noodles, gum, dairy products including ice-cream, soups, beverages, tea, drinks, alcoholic beverages, vitamin complex, etc can be added with the extract. In addition, the extract can be used in the production of powdered milk for infants, cosmetics, food additives, anti-diarrhea remedies, peritoneal dialysis agents, clinical nutrition agents, hygienic products for women, medicines for the eyes, gums, etc.

The present invention also provides a method for producing target protein comprising the following steps:

1) Preparing a plant expression vector containing target protein gene;

2) Preparing *Agrobacteria* genus microorganism transformed with the above expression vector;

3) Preparing a transformant expressing target protein by co-cultivation of the above *Agrobacteria* genus microorganism with plants or culture cells;

4) Culturing the above transformant; and

5) Isolating and purifying the target protein from the above transformant or the culture solution.

For the plant expression vector above, the present inventors used a plant expression vector expressing target protein using high-expressing peroxidase promoter (SWPA2) and especially in the preferred embodiments of the present invention, used a plant expression vector containing high-expressing peroxidase promoter (SWPA2), TEV (tobacco etch virus) leader sequence, signal sequence of calreticulin, human lactoferrin gene and CaMV 35S transcription terminator in order to express human lactoferrin as a target protein.

For the plants above, tobacco or medicinal plants of Araliaceae family can be used. For the medicinal plant of Araliaceae family, one selected from a group consisting of Siberian ginseng, *Panax ginseng*, wild ginseng, *Aralia elata* and *Dendropanax morbifera* can be preferably used.

In the preferred embodiments of the present invention, the present inventors prepared a plant expression vector that can regulate the expression of human lactoferrin gene by using high-expressing peroxidase SWPA2 promoter and then transformed *Agrobacteria* genus microorganism with the vector in order to develop culture cell lines producing human lactoferrin in medicinal plant cell culture. Then, the present inventors prepared tobacco cell line (Accession No: KCTC 10218BP), ginseng cell line (Accession No: KCTC 10219BP) and Siberian ginseng cell line that produce human lactoferrin by co-cultivation of the *Agrobacteria* genus microorganism with tobacco BY-2, ginseng or Siberian ginseng. Cultured those cells in selection medium containing kanamycin and selected cells having resistance, which were cultured again. Selected transformed cell lines by PCR (see FIGS. 2A and 2B), and measured the amount of produced human lactoferrin in the transformed cell lines with ELISA using human lactoferrin antibody (see FIG. 2C). The content of the produced human lactoferrin was all different by cell lines and the range was 0.7%–2.7% out of total water-soluble protein in callus stage. Performed Southern blotting with some of those cell lines, resulting in the confirmation that human lactoferrin gene was introduced into tobacco chromosomal DNA, and did Northern blotting as well to confirm the expression of human lactoferrin gene. Investigated if human lactoferrin protein was produced in tobacco culture cell line by Western blotting, resulting in the confirmation that 80-kDa human lactoferrin protein and 40-kDa partial human lactoferrin protein were produced (see FIG. 3C). The amount of human lactoferrin produced in suspension culture cells took 3–5% of total produced water-soluble protein (see FIGS. 4B and 4C).

Selected ginseng callus having resistance against kanamycin with the same method as that used for tobacco BY-2, after which confirmed the transformation by PCR. Investigated the content of human lactoferrin in those ginseng culture cells in callus stage, resulting in the confirmation that the content of the produced human lactoferrin took 0.07–3.0% of total water-soluble protein (see FIGS. 5B and 5C). Performed Southern blotting with some of those cell lines, resulting in the confirmation that human lactoferrin gene was successfully introduced into ginseng chromosomal DNA. Also confirmed that the expression of human lactoferrin gene by Northern blotting. Investigated if human lactoferrin protein was produced in ginseng culture cell lines by Western blotting, resulting in the confirmation that 80 kDa of whole human lactoferrin protein and 40 kDa of partial human lactoferrin protein were produced (see FIG. 6C).

Again, selected Siberian ginseng culture cells having resistance against kanamycin with the same method as that used for the selection of tobacco and ginseng culture cells, after which confirmed the transformation by PCR. Investigated the content of human lactoferrin in the transformed Siberian ginseng culture cells in callus stage (see FIGS. 7B and 7C), resulting in the confirmation that the content of human lactoferrin took 0.5–1.7% of total water-soluble protein. Performed Southern blotting with some of those cell lines, resulting in the confirmation that human lactoferrin gene was successfully introduced into chromosomal DNA of Siberian ginseng. Confirmed the expression of human lactoferrin gene by Northern blotting as well. Investigated if human lactoferrin protein was produced in Siberian ginseng culture cell lines by Western blotting, resulting in that 80 kDa of whole human lactoferrin protein and 40 kDa of partial human lactoferrin protein were produced, which was the same result as the cases of tobacco and ginseng (see FIG. 8C). The amount of human lactoferrin produced in suspension culture cells took 5% of total produced water-soluble protein (see FIG. 9B).

The present inventors compared the method for producing human lactoferrin using high-expressing peroxidase promoter (SWPA2) with that using CaMV 35S promoter. When SWPA2 promoter was used, the content of human lactoferrin in the total produced protein was much higher than when other promoters were used. Precisely, when CaMV 35S promoter was used for the production of human lactoferrin, the amount of human lactoferrin took 1.8% of total water-soluble protein produced in transformed tobacco culture cell line (Mitra and Zhang, *Plant Physiol.*, 106, 977–981, 1994) and just 0.3% of total water-soluble protein produced in tobacco plant (Salmon et al., *Protein Express. Purif.*, 13, 127–135, 1998), which were both lower than when SWPA2 was used. When mas P2 promoter was used for the production of human lactoferrin in the transformed potato (Chong et al., *Transgenic Research*, 9, 71–78, 2000), the content of human lactoferrin in the total water-soluble protein was 0.1%, which was also lower than when SWPA2 was used (see Table 1).

As seen hereinbefore, the present inventors developed tobacco BY-2, ginseng and Siberian ginseng culture cell lines producing human lactoferrin highly, which are transformed plant culture cell lines producing higher content of human lactoferrin than others reported ever. The plant culture cell lines of the present invention producing human lactoferrin highly can be effectively used as industrial plant culture cell lines producing human lactoferrin and for the production of novel functional health food enhancing immunity.

BRIEF DESCRIPTION OF THE DRAWINGS

The application of the preferred embodiments of the present invention is best understood with reference to the accompanying drawings, wherein.

SWPA2 promoter: Culture cell high-expressing peroxidase promoter,

TEV: TEV (tobacco etch virus) leader sequence,

ER: Signal sequence of calreticulin, 35S 3': CaMV 35S transcription terminator

Figure 2A:
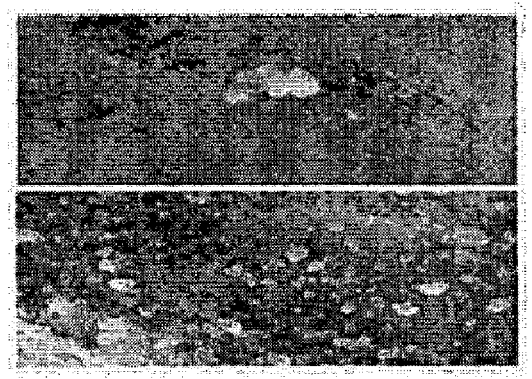
Figure 2B:
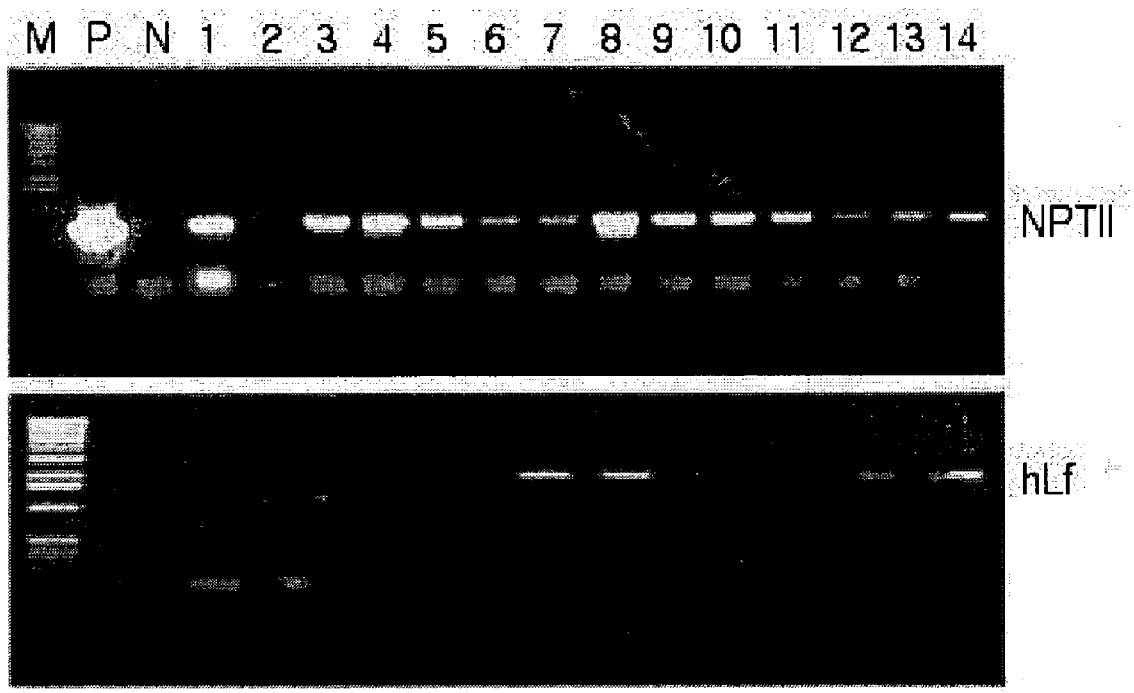
Figure 2C:
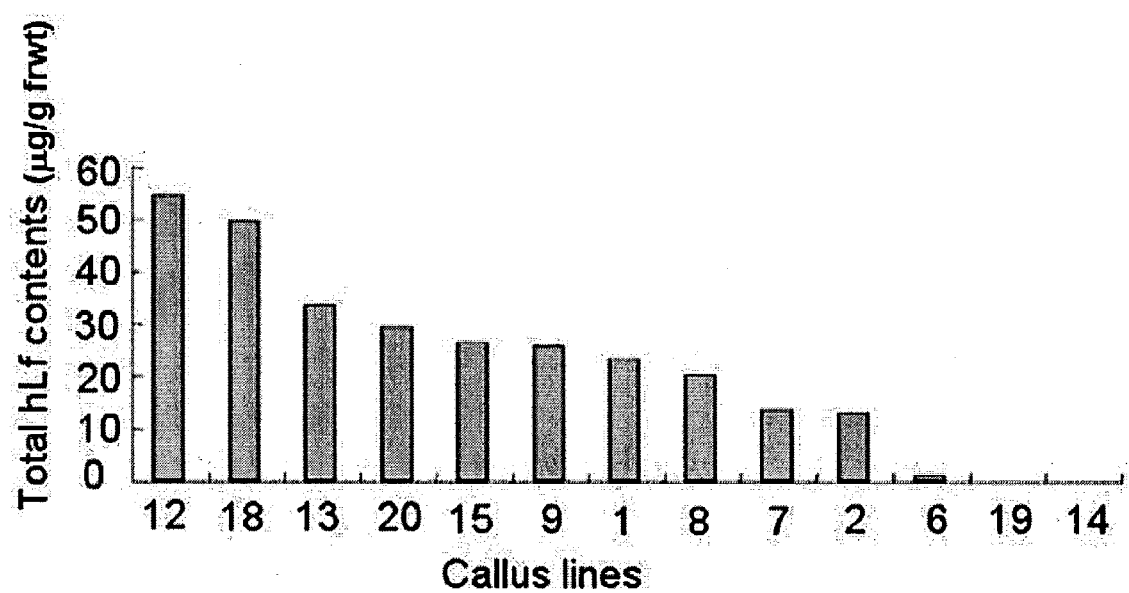
Figure 3A:
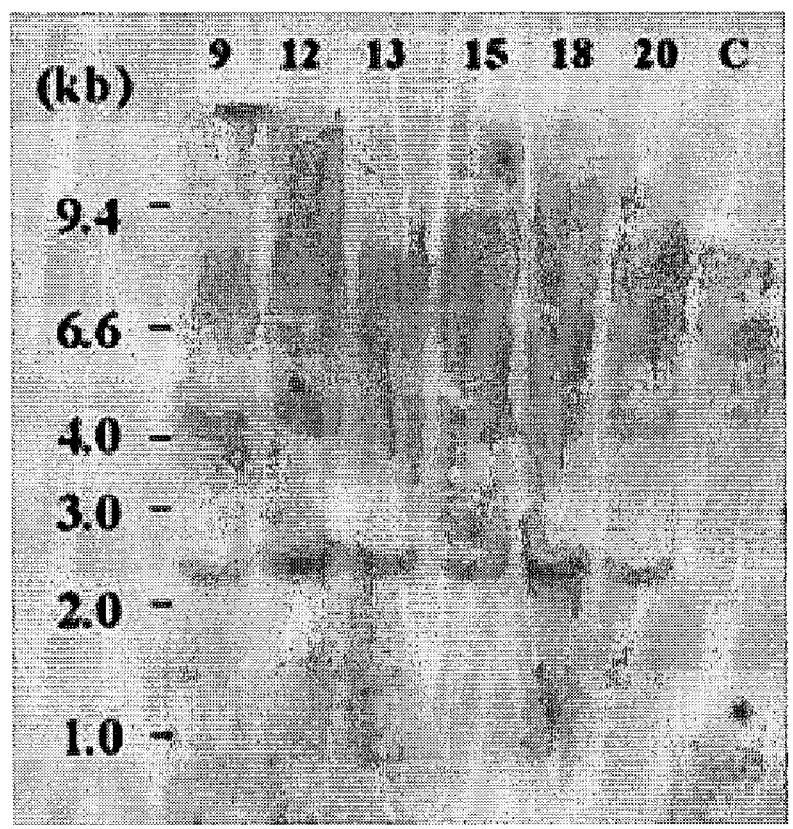

FIG. 2A is a set of photographs showing that transformed tobacco culture cells of the present invention are being developed to clusters on selection medium containing kanamycin;

FIG. 2B is a set of photographs showing the introduction of kanamycin and human lactoferrin gene, which was confirmed by PCR;

FIG. 2C is a graph showing the content of human lactoferrin in transformed tobacco calli;

FIG. 3A is a photograph showing the result of Southern blot analysis on the introduction of human lactoferrin gene into tobacco culture cell lines of the present invention;

9, 12, 13, 15, 18, 20: Transformed tobacco BY-2 cell lines,

C: Non-transformed tobacco BY-2 cell line

Figure 3B:
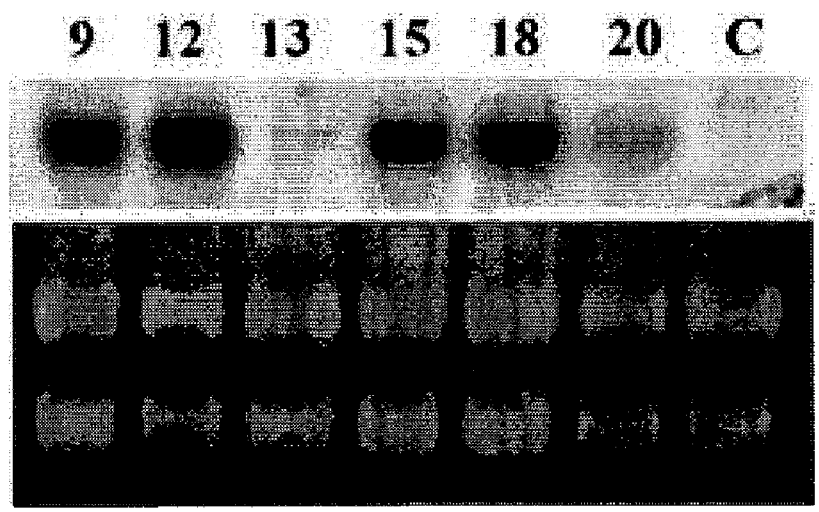

FIG. 3B is a set of photographs showing the result of Northern blot analysis on the expression of human lactoferrin in tobacco culture cell lines of the present invention;

9, 12, 13, 15, 18, 20: Transformed tobacco BY-2 cell lines,

C: Non-transformed tobacco BY-2 cell line

Figure 3C:
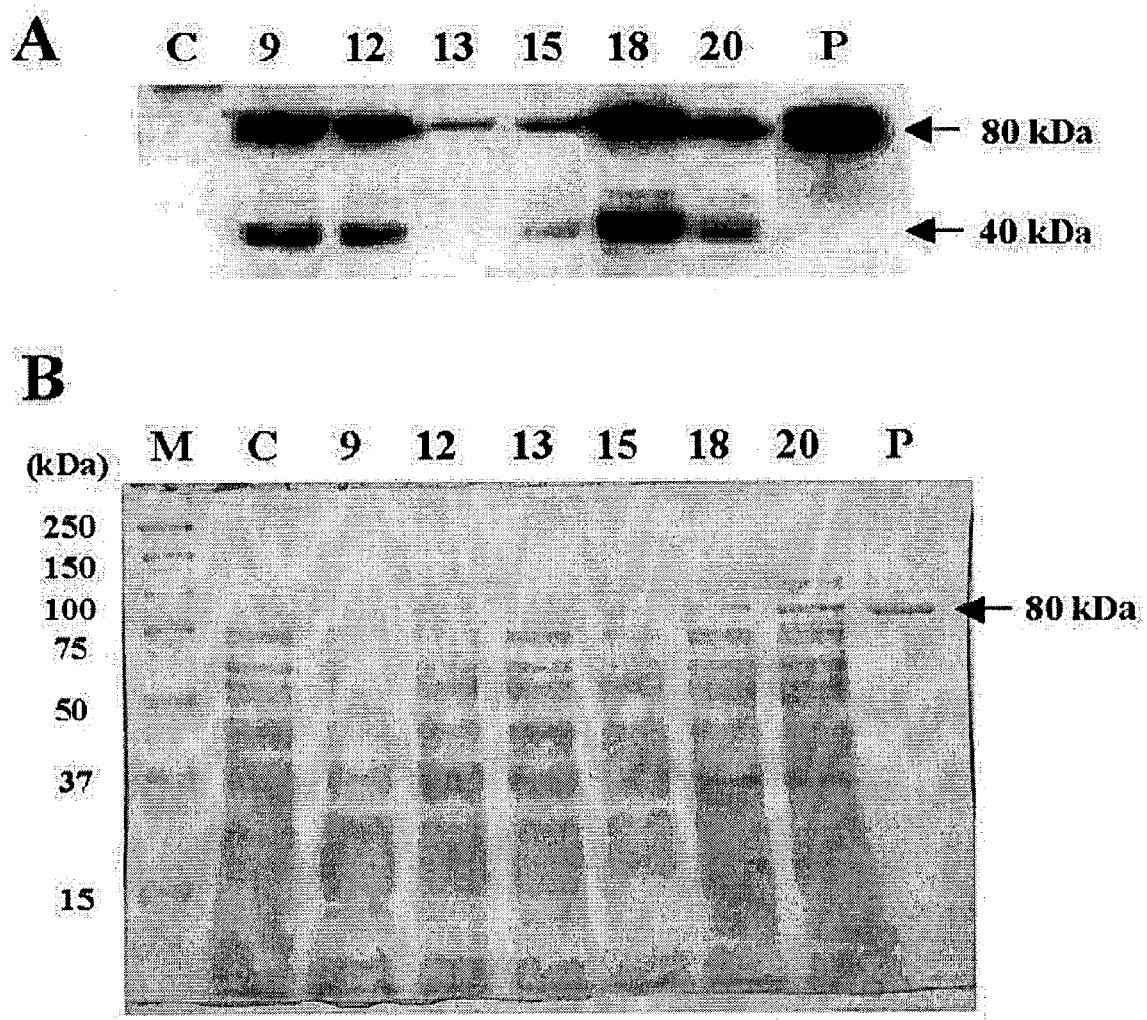

FIG. 3C is a set of photographs showing the result of Western blot analysis on the production of human lactoferrin protein in tobacco culture cell lines of the present invention;

9, 12, 13, 15, 18, 20: Transformed tobacco BY-2 cell lines,

C: Non-transformed tobacco BY-2 cell line,

P: Human lactoferrin standard protein (Sigma)

Figure 4A:
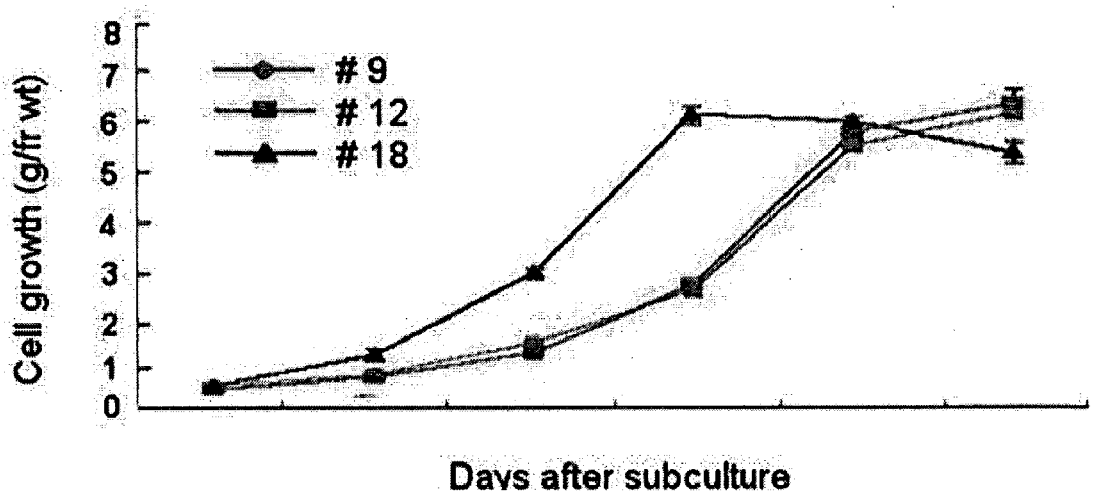
Figure 4B:
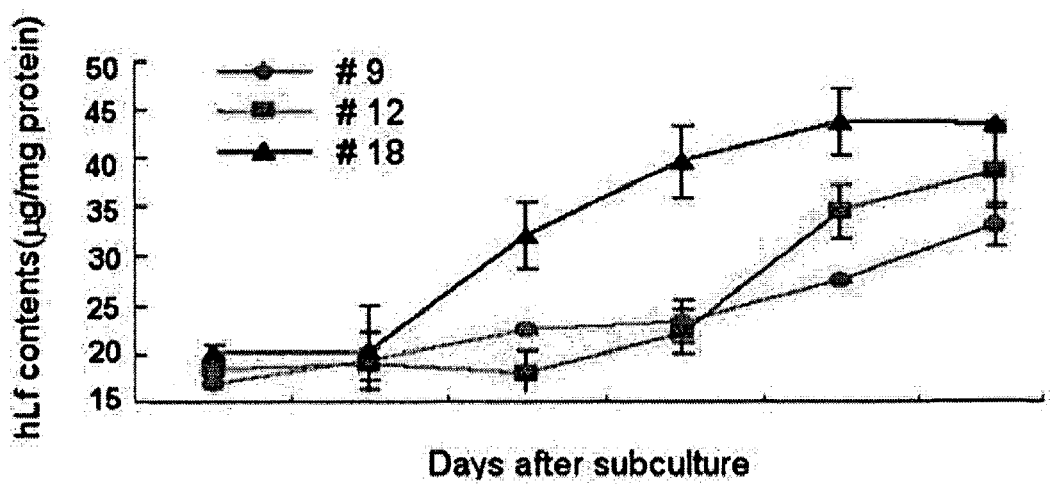
Figure 4C:
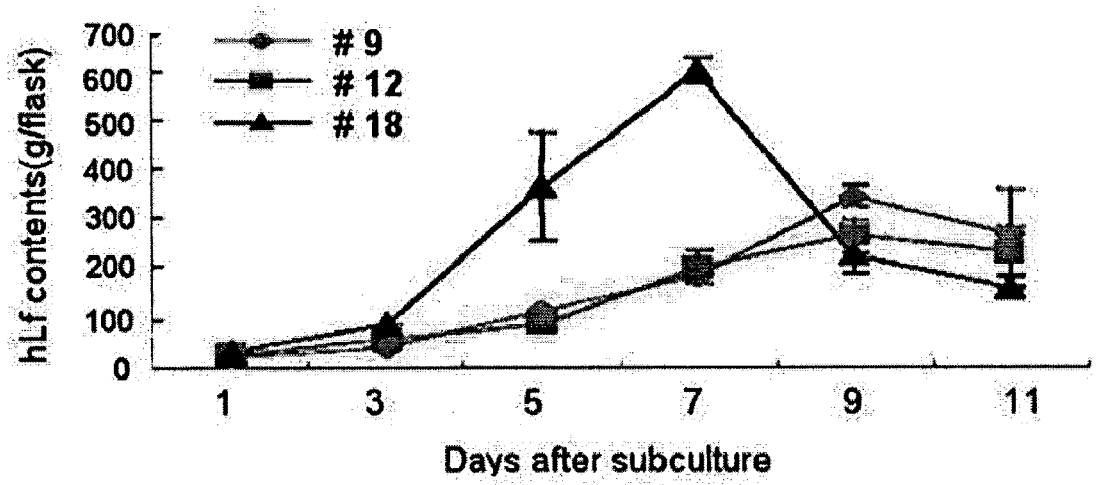
Figure 5A:
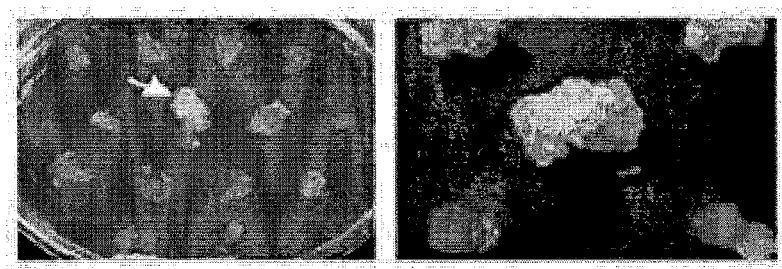
Figure 5B:
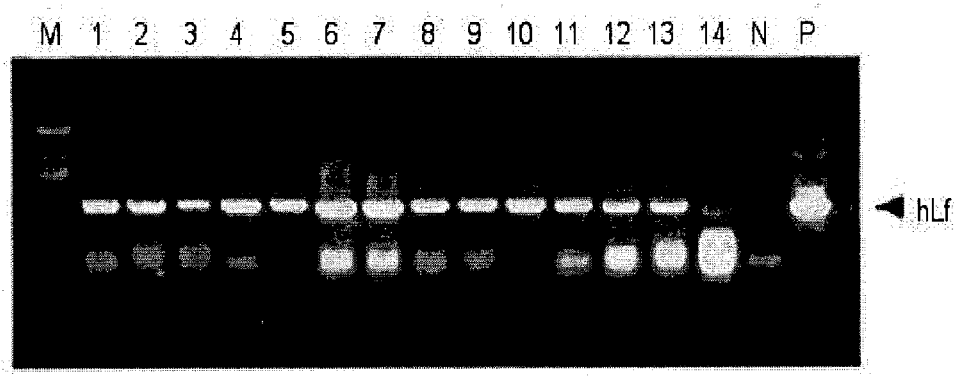
Figure 5C:
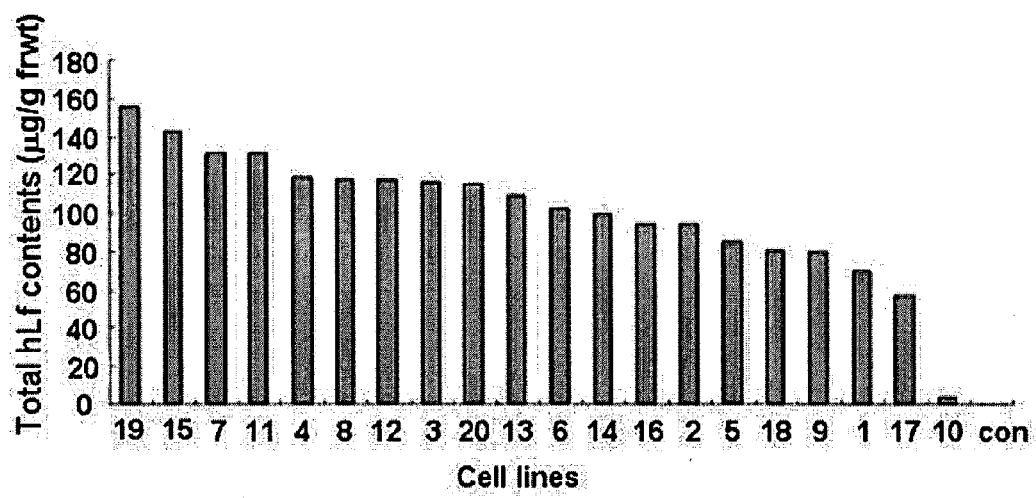
Figure 6A:
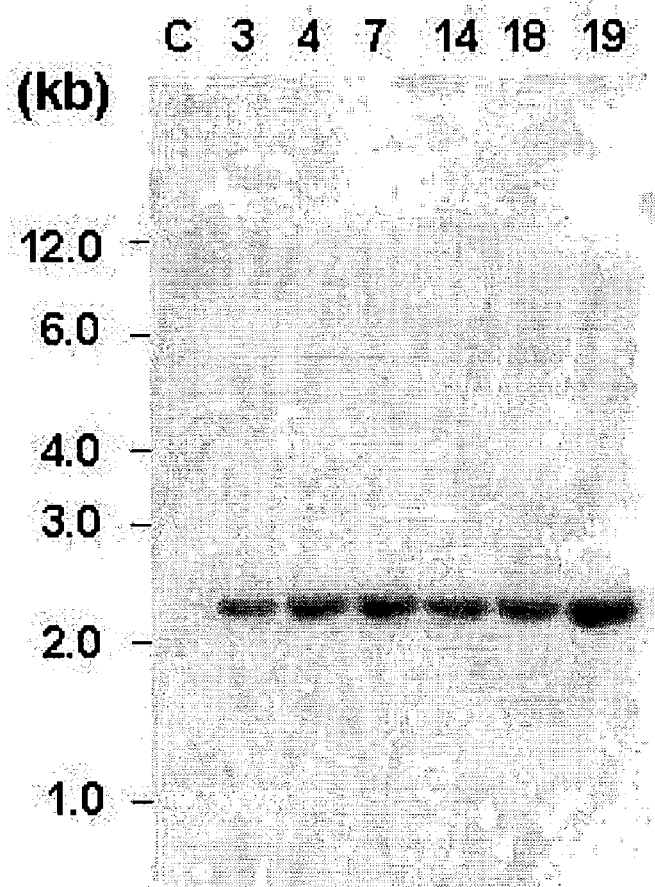

FIG. 4A is a graph showing the cell growth of the transformed tobacco culture cell lines of the present invention during suspension culture;

FIG. 4B is a graph showing the content of human lactoferrin produced in suspension cultured tobacco cell lines;

FIG. 4C is a graph showing the total content of human lactoferrin gathered from suspension cultured tobacco cell lines and media;

FIG. 5A is a set of photographs showing that the transformed ginseng culture cells of the present invention are being developed to clusters on selection medium containing kanamycin;

FIG. 5B is a photograph showing the introduction of human lactoferrin gene, which was confirmed by PCR;

FIG. 5C is a graph showing the content of human lactoferrin in transformed ginseng calli;

FIG. 6A is a photograph showing the result of Southern blot analysis on the introduction of human lactoferrin gene into ginseng culture cell lines of the present invention;

3, 4, 7, 14, 18, 19: Transformed ginseng cell lines,

C: Non-transformed ginseng cell line

Figure 6B:
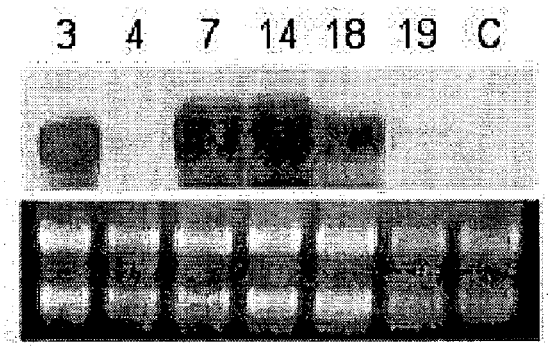

FIG. 6B is a set of photographs showing the result of Northern blot analysis on the expression of human lactoferrin in ginseng culture cell lines of the present invention;

3, 4, 71 14, 18, 19: Transformed ginseng cell lines,

C: Non-transformed ginseng cell line

Figure 6C:
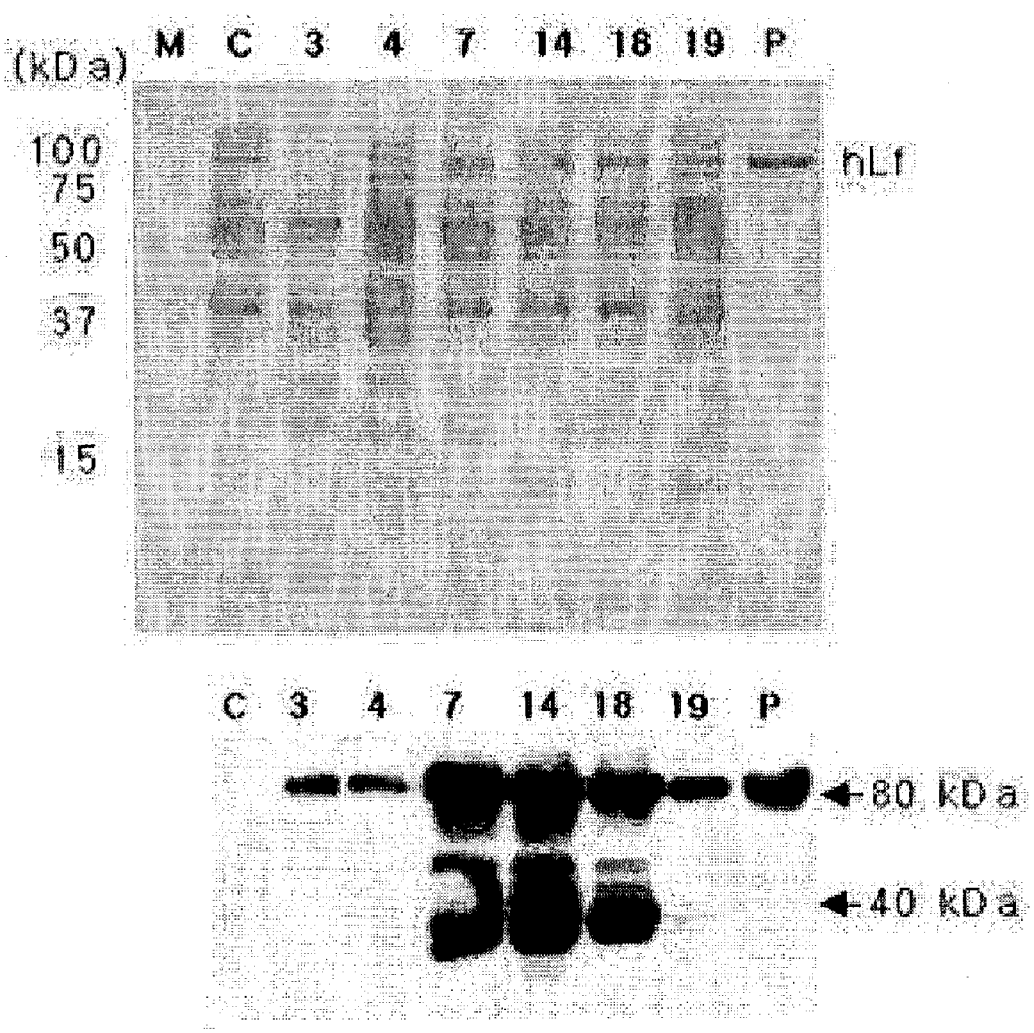

FIG. 6C is a set of photographs showing the result of Western blot analysis on the production of human lactoferrin protein in ginseng culture cell lines of the present invention;

3, 4, 7, 14, 18, 19: Transformed ginseng cell lines,

C: Non-transformed ginseng cell line,

P: Human lactoferrin standard protein (Sigma),

M: Marker

Figure 7A:
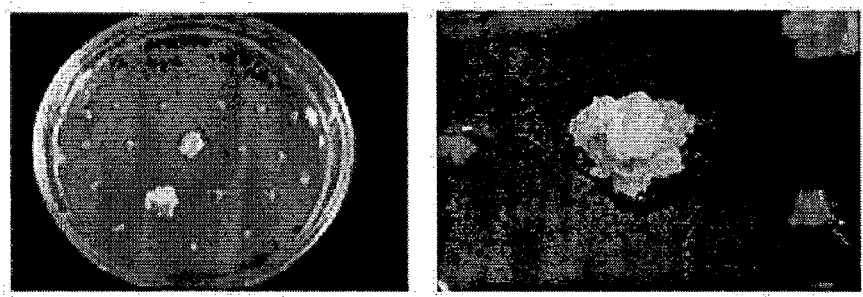
Figure 7B:
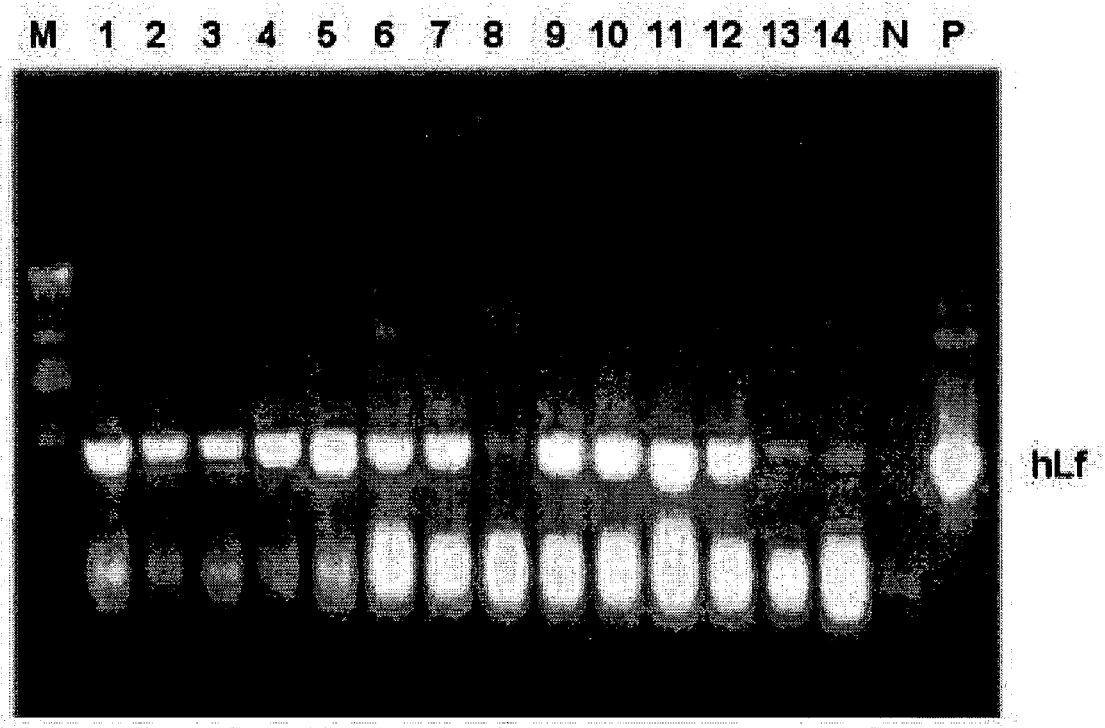
Figure 7C:
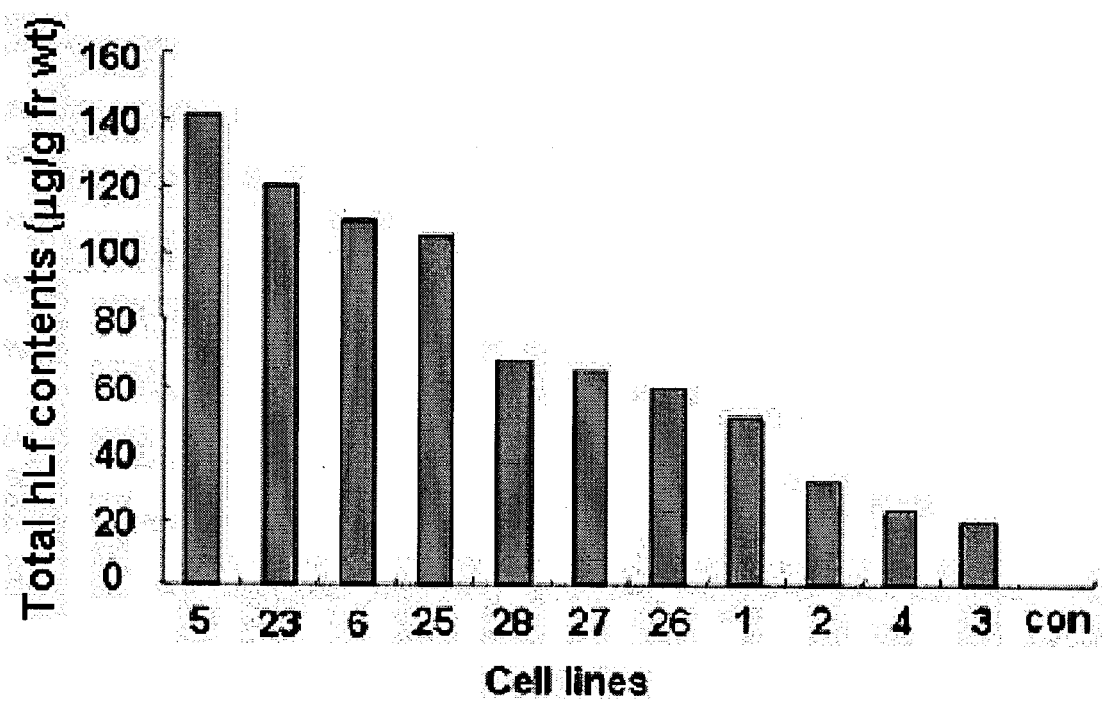
Figure 8A:
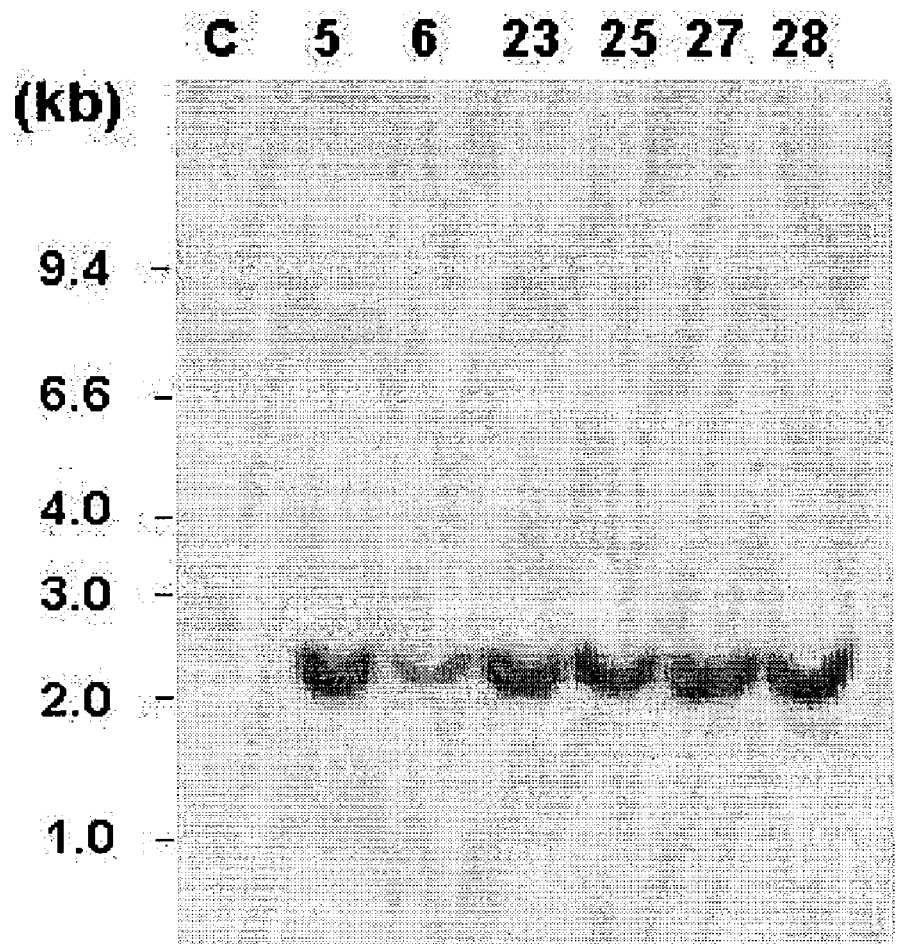

FIG. 7A is a set of photographs showing that the transformed Siberian ginseng culture cells of the present invention are being developed to clusters on selection medium containing kanamycin;

FIG. 7B is a photograph showing the introduction of human lactoferrin gene into transformed Siberian ginseng culture cell lines, which was confirmed by PCR;

FIG. 7C is a graph showing the content of human lactoferrin in callus stage of transformed Siberian ginseng culture cells;

FIG. 8A is a photograph showing the result of Southern blot analysis on the introduction of human lactoferrin gene into Siberian ginseng culture cell lines of the present invention;

5, 6, 23, 25, 27, 28: Transformed Siberian ginseng cell lines,

C: Non-transformed Siberian ginseng cell line

Figure 8B:
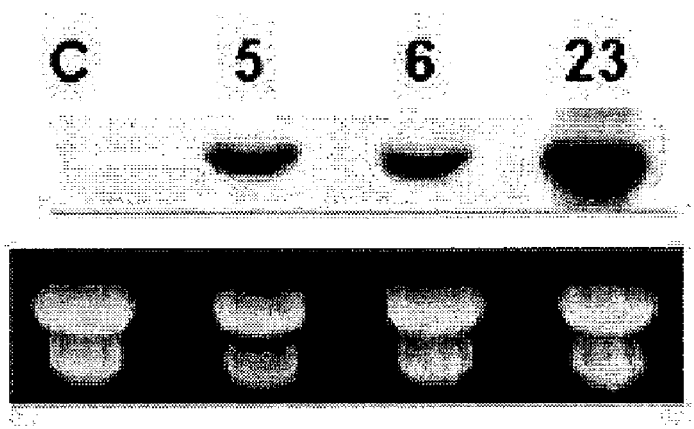

FIG. 8B is a set of photographs showing the result of Northern blot analysis on the expression of human lactoferrin in Siberian ginseng culture cell lines of the present invention;

5, 6, 23: Transformed Siberian ginseng cell lines,

C: Non-transformed Siberian ginseng cell line

Figure 8C:
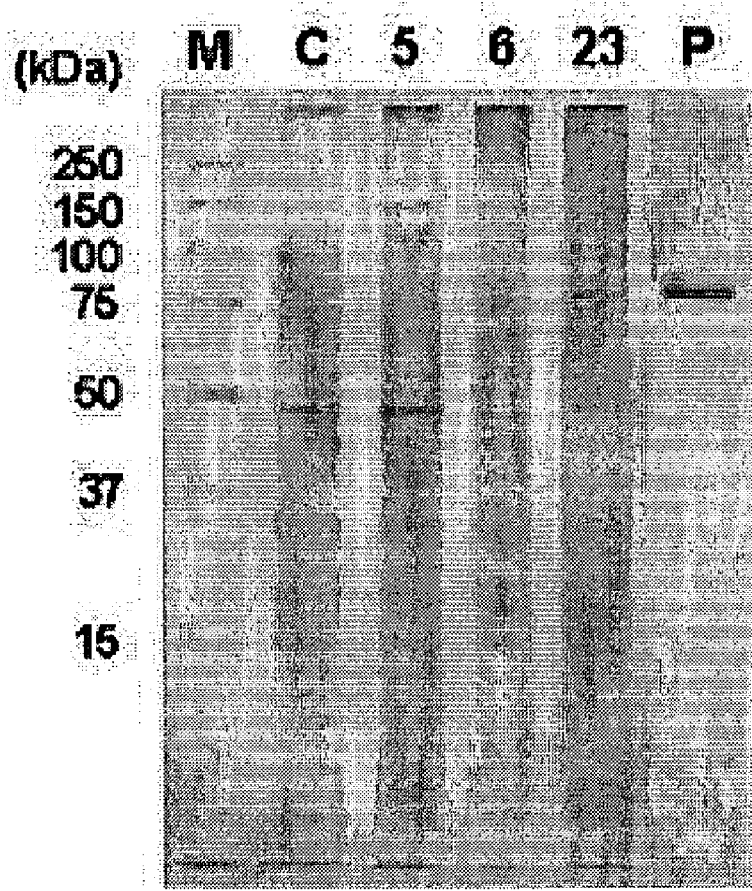
Figure 8C:
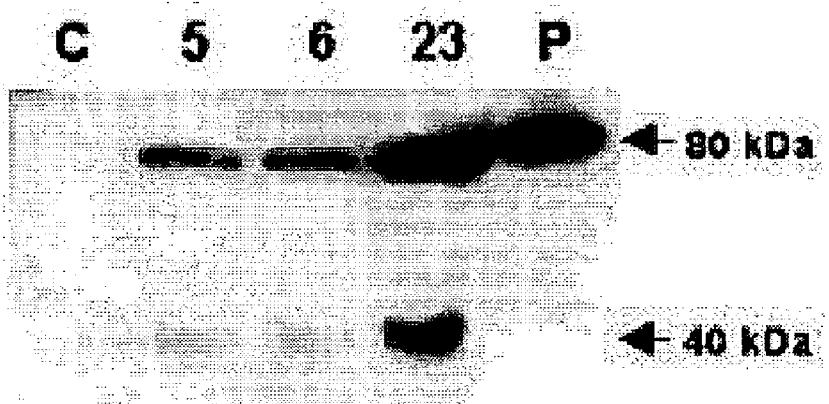

FIG. 8C is a set of photographs showing the result of Western blot analysis on the production of human lactoferrin protein in Siberian ginseng culture cell lines of the present invention;

5, 6, 23: Transformed Siberian ginseng cell lines,

C: Non-transformed Siberian ginseng cell line,

P: Human lactoferrin standard protein (Sigma),

M: Marker

Figure 9A:
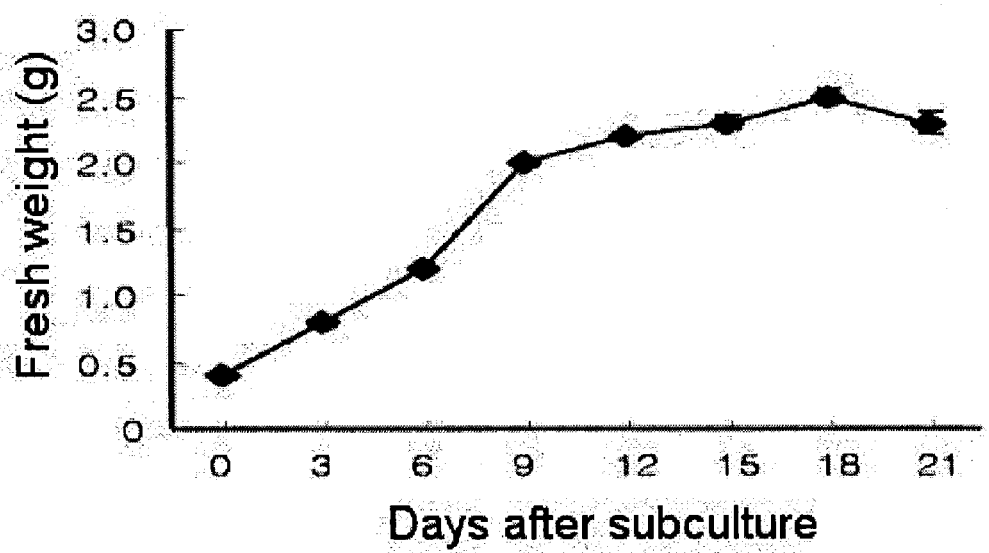
Figure 9B:
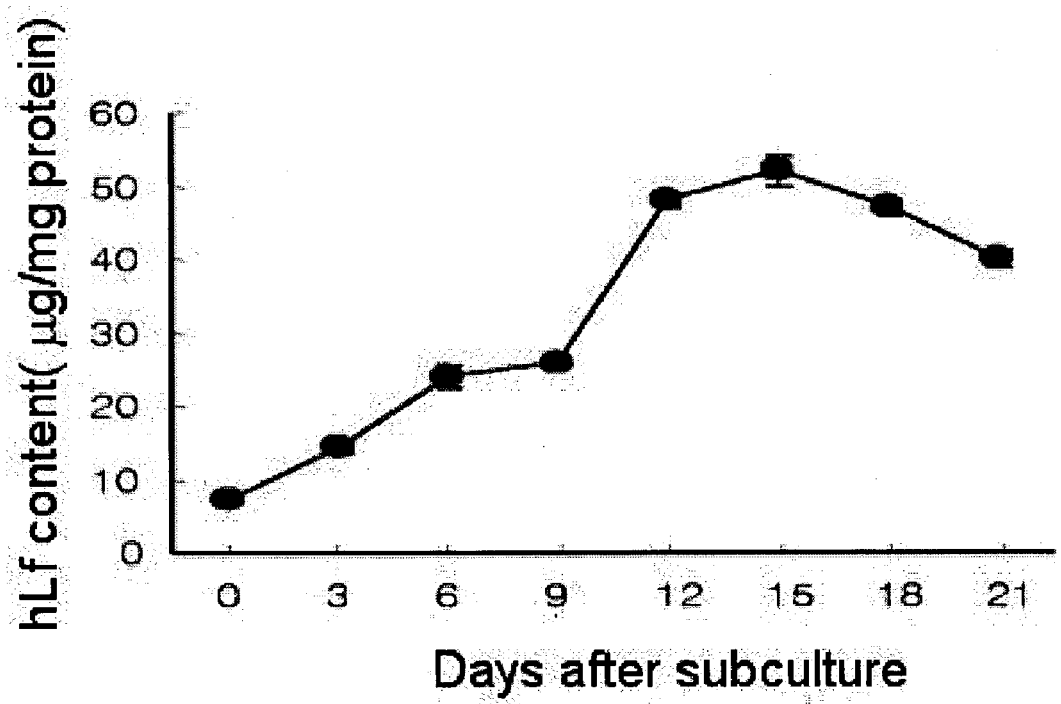

FIG. 9A is a graph showing the cell growth of the transformed Siberian ginseng culture cell lines during suspension culture;

FIG. 9B is a graph showing the content of human lactoferrin produced in suspension cultured Siberian ginseng cell lines.

EXAMPLES

Practical and presently preferred embodiments of the present invention are illustrative as shown in the following Examples. It will be appreciated, however, that those skilled in the art, on consideration of this disclosure, may make modifications and improvements within the spirit and scope of the present invention.

Example 1

Preparation of Plant Expression Vector Expressing Human Lactoferrin and Transformed Agrabacteria Genus Microorganism The present inventors prepared a plant expression vector that can mass-express human lactoferrin using high-expressing peroxidase promoter (SWPA2) and a transformant.

At first, cloned the base sequence coding signal peptide of calreticulin, known as a kind of endoplasmic reticulum (ER) protein of tobacco, by PCR in order to express human lactoferrin gene in cells. Used primers represented by SEQ. ID. No 1 and No 2, and tobacco cDNA library as a template for the PCR. For easy cloning, used primers having NcoI and SalI restriction enzyme sites.

N-terminal of human lactoferrin protein is the place where secretion signal is, which is to be removed for being combined with signal sequence of calreticulin prepared above. In order to do so, performed PCR using a primer represented by SEQ. ID. No 3 starting at $149^{th}$ base of human lactoferrin cDNA (U07643) and a 3'-end primer represented by SEQ. ID. No 4 as well. Cloned amplified 2.1 kb fragment into pGEM-T Easy vector (Promega, USA). Confirmed if human lactoferrin gene was correctly amplified by base sequencing, and then digested with restriction enzymes, SalI and XbaI.

Figure 1:
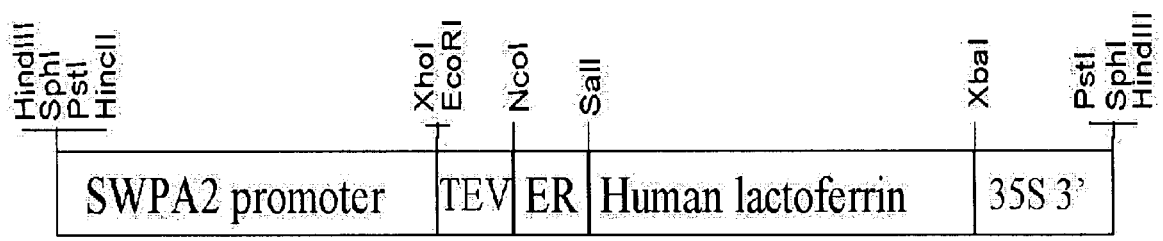
FIG. 1 is a diagram of a vector for transformation of the present invention that can express human lactoferrin protein in plant culture cells.

Prepared gene construct expressing human lactoferrin using the above fragments and high-expressing peroxidase promoter (SWPA2; PCT KR00/01231) (FIG. 1). Cut the gene construct with HindIII, which was inserted into pCGN1578 (McBride and Summerfelt, *Plant Mol. Biol.*, 14, 269–276, 1990) that was also cut by the same restriction enzyme, resulting in the preparation of a plant expression vector mass-expressing human lactoferrin.

The present inventors introduced the plant expression vector into *Agrobacterium tumefaciens* EHA101 to induce transformation of culture cells and named the *Agrobacterium* transformed with the plant expression vector "*Agrobacterium tumefaciens* EHA101 (SWPA2::hLf/pCGN1578)", which was deposited at Gene Bank of Korea Research Institute of Bioscience and Biotechnology on Apr. 3, 2002 (Accession No: KCTC 10217BP).

Example 2

Co-cultivation of *Agrobacteria* with Plant Materials

The present inventors prepared plants or culture cells mass-producing human lactoferrin by co-cultivation of the transformed *Agrobacteria* that was prepared in the above Example 1 with plants or culture cells.

Particularly, mixed suspension culture cells of tobacco, zygotic embryo of ginseng that were sub-cultured for 4 days and Siberian ginseng culture cells respectively with 100 μl of *Agrobacteria* culture solution that had been cultured on 5 ml LB medium containing 50 mg/L kanamycin in a shaking incubator, in a petri dish containing 10 ml of liquid medium, followed by co-cultivation in dark condition for 2 days. Transferred the co-cultured cells and zygotic embryos into a 15 ml centrifuge tube, and centrifuged (1000 rpm, 5 min, 25° C.) to remove *Agrobacteria*. Eliminated supernatants and then transferred into fresh MS medium (Murashige and Skoog, *Physiol. Plant.*, 15, 473–497, 1962), followed by centrifugation. Repeated the above procedure 4 times to wash the cells. After washing, co-cultured tobacco cells, zygotic embryos of ginseng and Siberian ginseng culture cells were cultured on MS medium (selection medium) containing 150 mg/L (for tobacco and Siberian ginseng) or 200 mg/L (for ginseng) of kanamycin, 250 mg/L of claforan and 0.1 mg/L of 2–4-D (1 mg/L for ginseng and Siberian ginseng), which were cultured in dark condition at 25° C.

Example 3

Preparation of Transformed Tobacco Culture Cell Lines Producing Human Lactoferrin The present inventors prepared transformed tobacco culture cell lines mass-producing human lactoferrin with the same method as used in the above Example 2.

Particularly, observed that tobacco BY-2 cells that were co-cultured with *Agrobacteria* prepared in the Example 1 were forming clusters on selection medium (MS medium, kanamycin 150 mg/L, claforan 250 mg/L, 2–4-D 0.1 mg/L) after 3–4 weeks of culture. Sub-cultured the cluster on fresh selection medium and selected proliferating clones (FIG. 2A).

Isolated chromosomal DNA from each callus showing resistance against kanamycin and performed PCR with specific primers of kanamycin resistant (nptII) and human lactoferrin (hLf) genes in order to confirm if transformation was completed. Used primers represented by SEQ. ID. No 5 and No 6 for kanamycin resistant gene, and primers represented by SEQ. ID. No 7 and No 8 for human lactoferrin gene.

As a result, specific bands of kanamycin resistant gene and human lactoferrin gene were observed at 0.7 kb and 2.7 kb in each callus showing resistance against kanamycin (FIG. 2B).

Example 4

Analysis of Human Lactoferrin Contents in Transformed Tobacco Culture Cell Lines The present inventors investigated human lactoferrin contents in 13 transformed tobacco cell lines prepared in the above Example 3 and confirmed to have human lactoferrin gene on the $21^{st}$ day of sub-culture on solid medium. For the analysis of human lactoferrin content, extracted water-soluble proteins from transformed tobacco callus using phosphate buffer (pH 7.0) and then analyzed thereof using Bioxytech Lactof-EIA™ Assay Kit (Oxis International, Inc.) according to the manufacturer's instructions.

As a result, human lactoferrin contents were vary from cell lines. #12 cell line showed 54.5 μg/g fr wt(54.5 μg of human lactoferrin was produced in 1 gram of transformed BY-2 cells), which was the highest human lactoferrin content of all, #18 cell line showed the second highest content 49.5 μg/g fr wt and #9 cell line followed with 33.6 μg/g fr wt (FIG. 2C).

Example 5

Analysis of Characteristics of Transformed Tobacco BY-2 Culture Cell Lines Producing Human Lactoferrin <5-1> Southern Blot Analysis The present inventors performed Southern blot analysis with 6 transformed tobacco BY-2 culture cell lines (#9, #12, #13, #15, #18, #20) prepared in the above Example 3 to confirm the introduction of foreign genes. According to the method of Dellaporta (Dellaporta, Newsletter, 57, 26–29, 1983), extracted genomic DNA from tobacco BY-2 culture cell lines. After digested 15 μg of the genomic DNA with restriction enzyme EcoRI, performed electrophoresis with the DNA on agarose gel. Transferred the genomic DNA on the above gel onto nylon membrane and then induced hybridization using gene fragment wherein 1 kb of human lactoferrin gene was labeled with $^{32}$P as a probe.

As a result, it was confirmed that every transformed tobacco BY-2 culture cell lines have human lactoferrin gene band, meaning that human lactoferrin gene was successfully introduced into tobacco BY-2 genome (FIG. 3A).

<5-2>

Northern Blot Analysis

The present inventors performed Northern blot analysis with 6 transformed tobacco BY-2 culture cell lines (#9, #12, #13, #15, #18, #20) to confirm the expression of human lactoferrin gene.

Particularly, extracted total RNA from tobacco culture cell lines using TRIzol™ (GIBCO/BRL) reagent, followed by electrophoresis with 15 μg of the RNA on agarose gel. Transferred the RNA on the gel onto nylon membrane and then induced hybridization using gene fragment wherein 1 kb of human lactoferrin gene was labeled with $^{32}$P as a probe.

As a result, 2.3 kb of human lactoferrin transcript was expressed in transformed tobacco BY-2 culture cell lines. Human lactoferrin gene was strongly expressed in #9, #12, #15, and #18 cell lines and weakly expressed in other cell lines (FIG. 3B).

<5-3> Western Blot Analysis

The present inventors performed Western blot analysis with transformed tobacco BY-2 culture cell lines to confirm the production of human lactoferrin therein.

Particularly, extracted total water-soluble proteins and denatured thereof. Performed electrophoresis with the proteins on 10% polyacrylamide gel and then fixed thereof on nitrocellulose membrane. Reacted the membrane with peroxidase-conjugated human lactoferrin antibody (Rabbit anti-Human Lactoferrin, BIODESIGN International), after which confirmed the production of human lactoferrin using ECL plus Western blotting screening system (Amersham Pharmacia Biotech UK Limited).

As a result, it was confirmed that 80 kDa and 40 kDa-sized human lactoferrin were produced in #9, #12 and #18 cell lines (FIG. 3C). In regard to the production of human lactoferrin from plants or plant cell cultures, there have been reports that 48 kDa human lactoferrin-derivative peptide was produced (1.8% of total water-soluble proteins) in transformed tobacco cell culture (Mitra and Zhang, Plant Physiol., 106, 977–981, 1994), 80 kDa human lactoferrin was produced in potato (Chong et al., Transgenic Res., 9, 71–78, 2000), 80 kDa and 53 kDa human lactoferrin were produced in tobacco plant (Salmon et al., Protein Express. Purif., 13, 127–135, 1998), 42 kDa and 38 kDa partial human lactoferrin along with 80 kDa were produced in tobacco and potatoes (Liu et al., Research Report, Ministry of Science and Technology, Korea, 2000).

The present inventors named the tobacco culture cell line (#12) producing human lactoferrin "hLf tobacco BY2 cell line" and deposited the cell line at Gene Bank of Korea Research Institute of Bioscience and Biotechnology on Apr. 3, 2002 (Accession No: KCTC 10218BP).

Example 6

Production of Human Lactoferrin in Suspension Cultured Tobacco BY-2 Cells

In order to mass-produce human lactoferrin in tobacco culture cells, the present inventors suspension-cultured 3 tobacco cell lines (#9, #12, #18) that had higher human lactoferrin content in callus stage. Suspension-culture was carried out for 11 days in 20 ml of liquid medium whereto 0.4 g of cells were inoculated. During the culture, collected cells at 2-day intervals, which were vacuum-filtered. Extracted water-soluble proteins from culture cells and culture medium using phosphate buffer solution (pH 7.0) and measured human lactoferrin content therein using Bioxytech Lactof-EIA™ Assay Kit (Oxis International, Inc.).

As a result, the maximum cell growth of suspension-cultured cell line #9 and #12 was detected on the 11$^{th}$ day of culture (6.4 g and 6.7 g, respectively), so was cell line #18 on the 7$^{th}$ day (6.4 g) (FIG. 4A). In the meantime, the cell growth pattern of non-transformed tobacco BY-2 culture cell line was similar to the cell growth pattern seen in cell line #9 and #12. The content of human lactoferrin produced during the suspension culture tented to be increased as the culture went on, so that cell line #9 produced 33.0 μg/mg protein, cell line #12 produced 38.7 μg/mg protein and cell line #18 produced 43.6 μg/mg protein of human lactoferrin (FIG. 4B). High-expressing peroxidase promoter (SWPA2) used for the transformation is characterized by inducing high expression especially in late stages of cell culture (Kim et al., Plant Mol. Biol., 51, 831–838, 2003; PCT application No: PCT/KR00/01231), which was reflected in the culture of transformed tobacco culture cell lines, resulting in the confirmation that the expression reached the maximum point in the stationary stage of the cell culture. 0.4 mg/flask, 0.3 mg/flask and 0.6 mg/flask of human lactoferrin was produced respectively from cell line #9, #12 and #18 (FIG. 4C), which were corresponding to 3.6%, 4.3% and 4.7% of total water-soluble protein.

Example 7

Preparation of Ginseng Culture Cell Lines Producing Human Lactoferrin

The present inventors prepared transformed ginseng culture cell lines mass-producing human lactoferrin with the same method as used in the above Example 2.

Particularly, sterilized the surface of ginseng seeds. Took zygotic embryo off and prepared cotyledon explants of zygotic embryos. Co-cultured the cotyledon explants with Agrobacteria with the same method of the above Example 4. Cultured thereof on selection medium (MS medium, kanamycin 200 mg/L, claforan 250 mg/L, 2,4-D 1 mg/L) to select culture cell lines having resistance against kanamycin. From 4 weeks after the culture, callus was begun to be induced (FIG. 5A). Selected induced callus and extracted chromosomal DNA, followed by PCR using human lactoferrin gene primers represented by SEQ. ID. No 9 and No 10. As a result, it was confirmed that 780 bp DNA was synthesized in most cell lines wherein human lactoferrin gene was included (FIG. 5B).

Example 8

Analysis of Ginseng Culture Cell Lines Highly Producing Human Lactoferrin

The present inventors investigated human lactoferrin contents in 20 transformed ginseng culture cell lines confirmed to have human lactoferrin gene on the 21$^{st}$ day of subculture. Followed the same procedure as when tobacco BY-2 culture cell lines were used. The human lactoferrin contents in transformed ginseng culture cell lines were higher than those in tobacco BY-2 culture cell lines and 11 cell lines among them were proved to have over 100 μg/g fr wt human lactoferrin. #19 cell line showed 155.5 μg/g fr wt, which was the highest human lactoferrin content of all, #15 cell line showed the second highest content 142.5 μg/g fr wt and #7 cell line followed with 130.7 μg/g fr wt. They took 2.5%, 2.7% and 3.0% out of total water-soluble protein respectively (FIG. 5C).

The present inventors named the ginseng culture cell line (#19) producing human lactoferrin "hLf ginseng cell line" and deposited the cell line at Gene Bank of Korea Research Institute of Bioscience and Biotechnology on Apr. 3, 2002 (Accession No: KCTC 10219BP).

Example 9

Analysis of Characteristics of Transformed Ginseng Culture Cell Lines Producing Human Lactoferrin <9-1> Southern Blot Analysis The present inventors performed Southern blot analysis with 6 transformed ginseng culture cell lines (#3, #4, #7, #14, #18, #19) prepared in the above Example 7 to confirm the introduction of foreign genes. According to the method of Dellaporta (Dellaporta, Newsletter, 57, 26–29, 1983), extracted genomic DNA from ginseng culture cell lines. After digested 15 μg of the genomic DNA with restriction enzyme ECORI, performed electrophoresis with the DNA on agarose gel. Transferred the genomic DNA on the above gel onto nylon membrane and then induced hybridization using gene fragment wherein 1 kb of human lactoferrin gene was labeled with $^{32}$P as a probe.

As a result, it was confirmed that every transformed ginseng culture cell lines have human lactoferrin gene band, meaning that human lactoferrin gene was successfully introduced into ginseng genome (FIG. 6A).

<9-2> Northern Blot Analysis

The present inventors performed Northern blot analysis with 6 transformed ginseng culture cell lines (#3, #4, #7, #14, #18, #19) using the same method as the above Example <5-2> to confirm the expression of human lactoferrin gene. Particularly, extracted total RNA from ginseng culture cell lines using TRIzol™ (GIBCO/BRL) reagent, followed by electrophoresis with 15 μg of the RNA on agarose gel. Transferred genomic DNA on the gel onto nylon membrane and then induced hybridization using gene fragment wherein 1 kb of human lactoferrin gene was labeled with $^{32}$P as a probe.

As a result, 2.3 kb of human lactoferrin transcript was expressed in transformed ginseng culture cell lines. Human lactoferrin gene was strongly is expressed in #3, #7, #14, and #18 cell lines and weakly expressed in other cell lines (FIG. 6B).

<9-3> Western Blot Analysis

The present inventors performed Western blot analysis with transformed ginseng culture cell lines using the same method as the above Example <5-3> to confirm the production of human lactoferrin protein therein. Particularly, extracted total water-soluble proteins and denatured thereof. Performed electrophoresis with the proteins on 10% polyacrylamide gel and then fixed thereof on nitrocellulose membrane. Reacted the membrane with peroxidase-conjugated human lactoferrin antibody (Rabbit anti-Human Lactoferrin, BIODESIGN International), after which confirmed the production of human lactoferrin using ECL plus Western blotting screening system (Amersham Pharmacia Biotech UK Limited).

As a result, it was confirmed that 80 kDa and 40 kDa-sized human lactoferrin were produced in #7, #14 and #18 cell lines (FIG. 6C). It was reported that plants and culture cells into which human lactoferrin gene was introduced produced whole size human lactoferrin or at least one of partial human lactoferrin.

Example 10

Preparation of Siberian Ginseng Culture Cell Lines Producing Human Lactoferrin The present inventors prepared transformed Siberian ginseng culture cell lines mass-producing human lactoferrin with the same method as the above Example 2. Particularly, co-cultured Siberian ginseng culture cells with *Agrobacteria* using the same method as used in the above Example 2. Cultured thereof on selection medium (MS medium, kanamycin 200 mg/L, claforan 250 mg/L, 2,4-D 1 mg/L) to select culture cell lines having resistance against kanamycin. From 4 weeks after the culture, callus was induced (FIG. 7A). Selected the kanamycin-resistant calli and extracted chromosomal DNA from them, followed by PCR using human lactoferrin gene primers represented by SEQ. ID. No 9 and No 10. As a result, it was confirmed that 780 bp DNA was synthesized in most cell lines wherein human lactoferrin gene was included (FIG. 7B).

Example 11

Analysis of Siberian Ginseng Culture Cell Lines Highly Producing Human Lactoferrin The present inventors investigated human lactoferrin contents in transformed Siberian ginseng culture cell lines confirmed to have human lactoferrin gene on the 21$^{st}$ day of subculture. Followed the same procedure as when tobacco BY-2 and ginseng culture cell lines were used. As a result, it was confirmed that transformed Siberian ginseng culture cell line #5 produced 140 μg/g fr wt of human lactoferrin and #23 cell line produced 120 μg/g fr wt (FIG. 7C).

Example 12

Analysis of Characteristics of Transformed Siberian Ginseng Culture Cell Lines Producing Human Lactoferrin <12-1> Southern Blot Analysis The present inventors performed Southern blot analysis with 6 transformed Siberian ginseng culture cell lines (#5, #6, #23, #25, #27, #28) prepared in the above Example 10 to confirm the introduction of foreign genes. Particularly, extracted genomic DNA from Siberian ginseng culture cell lines according to the method of Dellaporta (Dellaporta, Newsletter, 57, 26–29, 1983). After digesting 15 μg of the genomic DNA with restriction enzyme EcoRI, performed electrophoresis with the DNA on agarose gel. Transferred the genomic DNA on the above gel onto nylon membrane and then induced hybridization using gene fragment wherein 1 kb of human lactoferrin gene was labeled with $^{32}$P as a probe.

As a result, it was confirmed that every transformed Siberian ginseng culture cell lines have human lactoferrin gene band, meaning that human lactoferrin gene was successfully introduced into Siberian ginseng genome (FIG. 8A).

<12-2> Northern Blot Analysis

The present inventors performed Northern blot analysis with 3 transformed Siberian ginseng culture cell lines (#5, #6, #23) to confirm the expression of human lactoferrin gene. Particularly, extracted total RNA from Siberian ginseng culture cell lines using TRIzol™ (GIBCO/BRL) reagent, followed by electrophoresis with 15 μg of the RNA on agarose gel. Transferred genomic DNA on the gel onto nylon membrane and then induced hybridization using gene fragment wherein 1 kb of human lactoferrin gene was labeled with $^{32}$P as a probe.

As a result, 2.3 kb of human lactoferrin transcript was expressed in transformed ginseng culture cell lines. The expression level was higher in cell line #23, comparing to cell line #5 and #6 (FIG. 8B).

<12-3> Western Blot Analysis

The present inventors performed Western blot analysis with transformed Siberian ginseng culture cell lines to confirm the production of human lactoferrin protein therein. Particularly, extracted total water-soluble proteins and denatured thereof. Performed electrophoresis with the proteins on 10% polyacrylamide gel and then fixed thereof on nitrocellulose membrane. Reacted the membrane with peroxidase-conjugated human lactoferrin antibody (Rabbit) anti-Human Lactoferrin, BIODESIGN International), after which confirmed the production of human lactoferrin using ECL plus Western blotting screening system (Amersham Pharmacia Biotech UK Limited).

The result was similar to that of Northern blot analysis. That is, cell line #23 showed higher expression level than cell line #5 and #6. As in tobacco and ginseng culture cell lines, 80 kDa and 40 kDa-sized human lactoferrin were produced in Siberian ginseng culture cell lines (FIG. 8C).

Example 13

Production of Human Lactoferrin in Suspension Cultured Siberian Ginseng Cells

In order to mass-produce human lactoferrin in Siberian ginseng culture cells, the present inventors suspension-cultured Siberian ginseng cell line #23 that had higher human lactoferrin content in callus stage. Suspension-culture was carried out for 21 days in 20 ml of liquid medium whereto 0.4 g of cells were inoculated. During the culture, collected cells at 3-day intervals, which were vacuum-filtered. Extracted water-soluble proteins from culture cells and culture medium using phosphate buffer solution (pH 7.0) and measured human lactoferrin content therein using Bioxytech Lactof-EIA™ Assay Kit (Oxis International, Inc.).

As a result, the cell growth in suspension culture increased rapidly until the 9$^{th}$ day of culture and reached the maximum point of cell growth on the 18$^{th}$ of culture (FIG. 9A). Human lactoferrin content also increased during suspension culture but rather slowly increase until the 9$^{th}$ day of culture. After the 12$^{th}$ day of culture, human lactoferrin content increased rapidly and reached the maximum on the 15$^{th}$ day, suggesting that the produced human lactoferrin was more than 5% out of total water-soluble proteins (55 μg/mg protein) (FIG. 9B). The above result also suggests that the high-expressing peroxidase promoter, SWPA2, used for transformation induces high expression especially in late stages of cell culture (PCT application #PCT/KR00/01231).

Comparative Example 1

Comparison of the Amount of Expressed Human Lactoferrin

The present inventors compared two different methods for producing human lactoferrin: one is to use SWPA2, a high-expressing peroxidase promoter of the present invention and the other is to use CaMV 35S promoter.

As a result, it was confirmed that human lactoferrin was produced greatly when SWPA2 promoter of the present invention was used, comparing to when CaMV 35S promoter or mas P2 promoter was used. Particularly, when CaMV 35S promoter was used for the production of human lactoferrin, the amount of human lactoferrin took 1.8% of total water-soluble protein produced in transformed tobacco culture cell line (Mitra and Zhang, *Plant Physiol.*, 106, 977–981, 1994) and just 0.3% of total water-soluble protein produced in tobacco plant (Salmon et al., *Protein Express. Purif.*, 13, 127–135, 1998), which were both lower than when SWPA2 was used. When mas P2 promoter was used for the production of human lactoferrin in the transformed potato (Chong et al., *Transgenic Research*, 9, 71–78, 2000), the content of human lactoferrin in the total water-soluble protein was 0.1%, which was also lower than when SWPA2 was used (Table 1).

TABLE 1

Comparison of human lactoferrin contents in transformed plants and culture cells

| | % hLf of TSP[a] | μg hLf/g fr wt | Promoter | Reference |
|---|---|---|---|---|
| Siberian ginseng callus | 1.1 | 85 | SWPA2 | Present invention |
| Siberian ginseng suspension culture cells | 5.0 | 160 | SWPA2 | Present invention |
| Ginseng callus | 2.4 | 115 | SWPA2 | Present invention |
| Tobacco BY-2 callus | 1.26 | 26 | SWPA2 | Present invention |
| Tobacco BY-2 suspension-culture cells | 3.5 | 101 | SWPA2 | Present invention |
| Tobacco BY-2 callus | 1.8 | 36 | C2aMV 35S | Mitra & Zhang, 1994 |
| Tobacco plant (Xanthi NC) | 0.3 | 6.0 | CaMV 35S[b] | Slamon et al., 1998 |

TABLE 1-continued

Comparison of human lactoferrin contents in transformed plants and culture cells

| | % hLf of TSP[a] | µg hLf/g fr wt | Promoter | Reference |
|---|---|---|---|---|
| Potato leaf and tuber | 0.1 | 23 | mas P2 | Chong et al., 2000 |
| Potato tuber | 0.04 | 1.38 | CaMV 35S | Liu et al., 2000 |
| Sweet potato | 0.07 | 4.5 | CaMV 35S | Liu et al., 2000 |
| Polished rice | — | 500 µg/g polished rice | Glutelin | Anzai et 2000 |

[a]TSP: Total water-soluble protein, hLf: Human lactoferrin,
[b]Enhanced CaMV 35S,
—:data not shown Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An *Agrobacteria* genus microorganism transformed with an expression vector comprising a SWPA2 promoter, tobacco etch virus (TEV) leader sequence, calreticulin signal sequence, a gene encoding lactoferrin and CaMV 35S transcription terminator, wherein the *Agrobacteria* genus microorganism is *Agrobacterium tumefaciens* EHA101 (SWPA2::hLf/pCGN1578) deposited under Accession No: KCTC 10217BP.

2. A transformant transfected with an *Agrobacteria* genus microorganism transformed with an expression vector comprising a SWPA2 promoter, tobacco etch virus (TEV) leader sequence, calreticulin signal sequence, a gene encoding lactoferrin and CaMV 35S transcription terminator, and producing human lactoferrin, wherein the transformant is hLf tobacco BY2 cell line deposited under Accession No: KCTC 10218BP.

3. A transformant transfected with an *Agrobacteria* genus microorganism transformed with an expression vector comprising a SWPA2 promoter, tobacco etch virus (TEV) leader sequence, calreticulin signal sequence, a gene encodina lactoferrin and CaMV 35S transcription terminator, and producing human lactoferrin, wherein the transformant is hLf ginseng cell line deposited under Accession No: KCTC 10219BP.

* * * * *

SEQUENCE LISTING

<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:
      Calreticulin up primer

<400> SEQUENCE: 1
ggccatggct actcaacgaa gg                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
      Calreticulin down primer

<400> SEQUENCE: 2
gtcgacctca gcggagacga ca                                              22

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Human
      lactoferrin up primer

<400> SEQUENCE: 3
gtcgacggcc gtaggagaag gag                                             23

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Human lactoferrin down primer

<400> SEQUENCE: 4
ggccatctag atcggtttta cttcctga                                28

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: nptII
      up primer

<400> SEQUENCE: 5
gaggctattc ggctatgact g                                       21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: nptII
      down primer

<400> SEQUENCE: 6
atcgggagcg gcgataccgt a                                       21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: hLf up
      primer

<400> SEQUENCE: 7
gtcgacggcc gtaggagaag gag                                     23

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: hLf down
      primer

<400> SEQUENCE: 8
ggccatctag atcggtttta cttcctga                                28

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: lactoferrin
      upstream primer

<400> SEQUENCE: 9
cggggctgga gacgtggctt ttat                                    24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: lactoferrin
      downstream primer

```
<400> SEQUENCE: 10
acggcggtgt ggcaggactt ct                                              22
```